US008273528B2

(12) United States Patent
Martienssen et al.

(10) Patent No.: US 8,273,528 B2
(45) Date of Patent: *Sep. 25, 2012

(54) METHODS AND COMPOSITIONS FOR DETERMINING METHYLATION PROFILES

(75) Inventors: Robert Martienssen, Cold Springs Harbor, NY (US); Eric J. Richards, St. Louis, MO (US); Zachary Lippmann, Cold Spring Harbor, NY (US); Vincent Colot, Paris (FR)

(73) Assignees: Cold Spring Harbor Laboratory, Cold Spring Harbor, NY (US); Washington University, St. Louis, MO (US)

( * ) Notice: Subject to any disclaimer, the term of this patent is extended or adjusted under 35 U.S.C. 154(b) by 550 days.

This patent is subject to a terminal disclaimer.

(21) Appl. No.: 11/654,058

(22) Filed: Jan. 16, 2007

(65) Prior Publication Data

US 2007/0178506 A1 Aug. 2, 2007

Related U.S. Application Data

(63) Continuation of application No. 10/606,502, filed on Jun. 26, 2003, now Pat. No. 7,186,512.

(60) Provisional application No. 60/392,071, filed on Jun. 26, 2002.

(51) Int. Cl.
*C12Q 1/68* (2006.01)
*C12P 19/34* (2006.01)
*C07H 21/02* (2006.01)
*C07H 21/04* (2006.01)

(52) U.S. Cl. ....... 435/6.1; 435/91.2; 536/23.1; 536/24.3

(58) Field of Classification Search .................. None
See application file for complete search history.

(56) References Cited

U.S. PATENT DOCUMENTS

| | | | |
|---|---|---|---|
| 5,405,760 A | 4/1995 | Raleigh et al. | |
| 5,786,146 A | 7/1998 | Herman et al. | |
| 5,871,917 A | 2/1999 | Duffy | |
| 6,200,756 B1 | 3/2001 | Herman et al. | |
| 6,265,171 B1 | 7/2001 | Herman et al. | |
| 6,331,393 B1 | 12/2001 | Laird et al. | |
| 6,605,432 B1 | 8/2003 | Huang | |
| 7,186,512 B2 | 3/2007 | Martienssen et al. | |
| 2001/0046669 A1 | 11/2001 | McCobmie et al. | |
| 2002/0123053 A1 | 9/2002 | Luo et al. | |
| 2003/0129602 A1 | 7/2003 | Huang | |
| 2003/0148290 A1 | 8/2003 | Cottrell | |
| 2003/0165923 A1 | 9/2003 | Li et al. | |
| 2003/0180779 A1 | 9/2003 | Lofton-Day et al. | |

FOREIGN PATENT DOCUMENTS

| WO | WO 00/26401 A1 | 5/2000 |
|---|---|---|
| WO | WO 00/50587 A1 | 8/2000 |
| WO | WO 01/68807 A2 | 9/2001 |
| WO | WO 01/75172 A1 | 10/2001 |
| WO | WO 03/025215 A1 | 9/2002 |
| WO | WO 03/023065 A1 | 3/2003 |
| WO | WO 03/027259 A2 | 4/2003 |
| WO | WO 03/035860 A1 | 5/2003 |
| WO | WO 03/066895 A2 | 8/2003 |
| WO | WO 03/076666 A1 | 9/2003 |
| WO | WO 2004/046313 A2 | 6/2004 |

OTHER PUBLICATIONS

Shiraishi, M. et al., PNAS USA, vol. 96, pp. 2913-2918 (1999).*
Craig, J. M. et al., Nature Genetics, vol. 7, pp. 376-382 (1994).*
Cross, S.H. et al., Nature Genetics, vol. 6, pp. 236-244 (1994).*
Adorjan, Peter et al.; "Tumour class prediction and discovery by microarray-based DNA methylation analysis"; *Nucleic Acids Research*, 2002, vol. 30, No. 5 e21, 9 pages.
Burman Robert W. et al.; "Hypomethylation of an Expanded FMR1 Allele Is Not Associated with a Global DNA Methylation Defect"; *Am. J. Hum. Genet.*, 1999, vol. 65, pp. 1375-1386.
Caldas, Carlos et al.; "Frequent somatic mutations and homozygous deletions of the p16 (*MTS1*) gene in pancreatic adenocarcinoma"; *Nature Genetics*, 1994, vol. 8, pp. 27-32.
Eads, Cindy A. et al.; "MethyLight: a high-throughput assay to measure DNA methylation"; *Nucleic Acids Research*, 2000, vol. 28, No. 8, e32, 8 pages.
Frigola, Jordi et al.; Methylome profiling of cancer cells by amplification of inter-methylated sites (AIMS)'; *Nucleic Acids Research*, 2002, vol. 30, No. 7, e28, 7 pages.
Genc, B. et al.; "Identification of disease associated genes and tumour class prediction by genome wide microarray-based DNA methylation scanning"; *The American Journal of Human Genetics*, 2001, vol. 69, No. 4, 1 page abstract.
Hatada, Izuho et al.; "A microarray-based method for detecting methylated loci"; *J. Hum. Genet*, 2002, Vo. 47, pp. 448-451.
Herman, James G. et al.; "Methylation-specific PCR: A novel PCR assay for methylation status of CpG islands"; *Proc. Natl. Acad. Sci.*, 1996, vol. 93, pp. 9821-9826.
Huang, Tim Hui-Ming et al.; "Methylation profiling of CpG islands in human breast cancer cells"; *Human Molecular Genetics*, 1999, vol. 8, No. 3, pp. 459-470.
McClelland, Michael et al.; "Effect of site-specific modification on restriction endonucleases and DNA modification methyltransferases"; *Nucleic Acids Research*, 1994, vol. 22, No. 17, pp. 3640-3659.
Oefner, "Efficient random sucloning of DNA sheared in a recirculating point-sink flow system", *Nucl. Acids Res.*, 1996, pp. 3879-3886, vol. 24.
Okamoto, Keisei et al.; "Epigenetic changes at the insulin-like growth factor II/H19 locus in developing kidney is an early event in Wilms tumorigenesis"; *Proc. Natl. Acad. Sci.*, 1997, vol. 94, pp. 5367-5371.
Schutte, Mieke et al.; "Abrogation of the Rb/p16 Tumor-suppressive Pathway in Virtually All Pancreatic Carcinomas"; *Cancer Research*, 1997, vol. 57, pp. 3126-3130.
Steigerwald, Sabine D. et al.; "Ligation-mediated PCR improves the sensitivity of methylation analysis by restriction enzymes and detection of specific DNA strand breaks"; *Nucleic Acids Research*, 1990, vol. 18, No. 6, pp. 1435-1439.

(Continued)

*Primary Examiner* — Teresa E Strzelecka

(74) *Attorney, Agent, or Firm* — Kilpatrick Townsend & Stockton LLP

(57) ABSTRACT

Methods and compositions for determining the methylation profile of individuals and using the profiles to identify clones with desired traits.

14 Claims, No Drawings

OTHER PUBLICATIONS

Tompa, Rachel et al.; "Genome-Wide Profiling of DNA Methylation Reveals Transposon Targets of Chromomethylase3"; *Current Biology*, 2002, vol. 12, pp. 65-68.

Toyota, Minoru et al.; "Identification of Differentially Methylated Sequences in Colorectal Cancer by Methylated CpG Island Amplification"; *Cancer Research*, 1999, vol. 59, pp. 2307-2312.

Wang, C.H. et al.; "Autism DNA methylation profiling using CpG microarrays"; *The American Journal of Human Genetics*, 2001, vol. 69, No. 4, 1 page abstract.

Wei, Susan H. et al.; "Methylation Microarray Analysis of Late-Stage Ovarian Carcinomas Distinguishes Progression-free Survival in Patients and Identifies Candidate Epigenetic Markers"; *Clinical Cancer Research*, 2002, vol. 8, pp. 2246-2252.

Yan, Pearlly S. et al. "CpG Island Arrays: An Application toward Deciphering Epigenetic Signatures of Breast Cancer"; 2000, *Clinical Cancer Research*, vol. 6, pp. 1432-1438.

HGM2002; Seventh International Human Genome Meeting, Apr. 2002, 1 page.

Yamada, Yoichi et al.; "A comprehensive analysis of Allelic Methylation Status of CpG islands on Human Chromosome 21q"; 2004, Genome Research, pp. 247-266.

Liang, Ganging et al.; "Identification of DNA methylation differences during tumorigenesis by methylation-sensitive arbitrarily primed polymerase chain reactions"; 2002, *Methods*, vol. 27, No. 2, pp. 150-155.

Singer-Sam, J. et al.; "A quantitative HpaII-PCR assay to measure methylation of DNA from a small number of cells"; 1990, *Nucleic Acids Research*, vol. 3, No. 18, p. 687.

Steensel, Van B. et al., "Chromatin profiling using targeted DNA adenine methyltransferase", 2001, *Nature Genetics*, vol. 27 No. 3, pp. 304-308.

Yan, Pearlly S. et al.; "CpG Island Arrays: An Application toward Deciphering Epigenetic Signatures of Breast Cancer"; 2000, *Clinical Cancer Research*, vol. 6, pp. 1432-1438.

Craig, B.A. et al.; "Designing Microarrays"; *Applied Statistics in Agriculture*, pp. 159-164., 2001.

McrBC—M0272—NEB Restriction Endonucleases; http://www.neb.com/neb/products/res_enzymes/272.html, 3 pages, 2004.

"McrBC"; Technical Bulletin, *New England Biolabs*, Inc., 2 pages, 2004.

Yamada, Yoichi et al.; "A comprehensive analysis of CpG islands reveals methylation imprints on human chromosome 21"; HGM2002 Workshop Abstract No. 13, 1 page., 2001.

Yamada, Yoichi et al.; "A comprehensive analysis of CpG islands reveals methylation imprints on human chromosome 21"; HGM2002 Poster No. 89, 1 page, 2001.

PowerPoint entitled "Genome wide analysis of DNA methylation using microarrays" (prepared Feb. 2001; unpublished).

Chu, Da-Chang et al.; "The Use of Real-Time Quantitative Polymerase Chain Reaction to Detect Hypermethylation of the CPG Islands in the Promoter Region Flanking the GSTP1 Gene to Diagnose Prostrate Carcinoma"; 2002, *The Journal of Urology*, vol. 167, pp. 1854-1858.

Davey, Colin et al.; "CpG Methylation Remodels Chromatin Structure in vitro"; 1997, *Journal of Molecular Biology*, vol. 267, No. 2, pp. 276-288.

Herfarth, Klaus K.F. et al.; "A Specific CpG Methylation Pattern of the MGMT Promoter Region Associated with Reduces MGMT Expression in Primary Colorectal Cancers"; 1999, *Molecular Carcinogenesis*, vol. 24, No. 2, pp. 90-98.

Li, Long-Cheng et al.; "Methylation of the E-Cadherin Gene Promoter Correlates with Progression of Prostate Cancer"; 2001, *The Journal of Urology*, vol. 166, pp. 705-709.

Weber, Michael et al.; "Extensive tissue-specific variation of allelic methylation in the Igf2 gene during mouse fetal development: relation to expression and imprinting"; 2001, *Mechanisms of Development*, vol. 101, No. 1-2, pp. 133-141.

* cited by examiner

METHODS AND COMPOSITIONS FOR DETERMINING METHYLATION PROFILES

CROSS-REFERENCE TO RELATED APPLICATIONS

This application is a Continuation Application of U.S. patent application Ser. No. 10/606,502, filed Jun. 26, 2003, now issued U.S. Pat. No. 7,186,512, which claims benefit of priority to U.S. Provisional Application No. 60/392,071, filed Jun. 26, 2002, both of which are incorporated by reference for all purposes.

STATEMENT AS TO RIGHTS TO INVENTIONS MADE UNDER FEDERALLY SPONSORED RESEARCH AND DEVELOPMENT

This invention was made with Government support under Grant No. NSF 0077774, awarded by the National Science Foundation. The government has certain rights in this invention.

FIELD OF THE INVENTION

The present invention relates to determination of methylation profiles.

BACKGROUND OF THE INVENTION

DNA methylation is a ubiquitous biological process that occurs in diverse organisms ranging from bacteria to humans. During this process, DNA methyltransferases catalyze the post-replicative addition of a methyl group to the N6 position of adenine or the C5 or N4 position of cytosine, for which S-adenosylmethionine is the universal donor of the methyl group. In higher eukaryotes, DNA methylation plays a role in genomic imprinting and embryonic development. In addition, aberrations in DNA methylation have been implicated in aging and various diseases including cancer.

Therefore, there is a need for methods of determining the methylation profile of an individual cell or organism. The present invention addresses this and other problems.

BRIEF SUMMARY OF THE INVENTION

The present invention provides methods for determining a methylation profile of a cell, tissue, or organism. In some embodiments, the methods comprise the steps of:

a. providing a uniformly-sized population of randomly cleaved or sheared DNA from the cell, tissue, or organism, wherein the DNA comprises a first portion and a second portion and each portion comprises methylated and unmethylated nucleotides;

b. separating the second portion into a methylated DNA sub-portion and an unmethylated DNA sub-portion;

c. quantifying the relative amount of at least one specific sequence in at least two DNA samples selected from the group consisting of the first portion, the methylated DNA sub-portion, and the unmethylated DNA sub-portion, thereby determining the methylation profile of several such nucleic acid sequences from the cell or organism.

In some embodiments, the methods comprise the steps of:
labeling the at least two DNA samples with different labels, and
hybridizing the at least two DNA samples to a nucleic acid; and
determining the relative hybridization of the at least two DNA samples to the specific sequence by calculating the ratio of the two hybridizing labels.

In some embodiments, the quantifying step comprises quantitative amplification.

In some embodiments, the at least two DNA samples are the methylated DNA sub-portion and the unmethylated DNA sub-portion. In some embodiments, the at least two DNA samples are the first portion and the methylated DNA sub-portion. In some embodiments, the at least two DNA samples are the first portion and the unmethylated DNA sub-portion.

In some embodiments, the randomly cleaved or sheared DNA comprises methylated and unmethylated recognition sequences of a methyl-sensitive restriction enzyme and the separating step comprises cleaving the second portion with the methyl-sensitive restriction enzyme. In some embodiments, the randomly cleaved or sheared DNA comprises methylated and unmethylated recognition sequences of a methyl-dependent restriction enzyme and the separating step comprises cleaving the second portion with the methyl-dependent restriction enzyme.

In some embodiments, the nucleic acid is linked to a solid support. In some embodiments, the solid support is a microarray. In some embodiments, the solid support is a bead. In some embodiments, the solid support is a matrix.

In some embodiments, the organism is a plant. In some embodiments, the organism is a fungus. In some embodiments, the organism is a prokaryote. In some embodiments, the prokaryote is a bacterial pathogen. In some embodiments, the bacterial pathogen is selected from the group consisting of gram positive and gram negative species and mycobacteria. In some embodiments, the organism is an animal. In some embodiments, the animal is a human.

In some embodiments, the cell is a stem cell. In some embodiments, the cell is transgenic and the nucleic acid corresponds to the insertion site of a transgene. In some embodiments, the tissue is blood. In some embodiments, the tissue is biopsy tissue. In some embodiments, the tissue is resected tissue. In some embodiments, the tissue is normal.

In some embodiments, the tissue is tumor tissue. In some embodiments, the tissue is precancerous.

In some embodiments, the methods further comprise comparing the methylation profile of a nucleic acid with the transcription of the nucleic acid, thereby determining the relation between methylation and transcription of the nucleic acid. In some embodiments, the transcription of the nucleic acid is detected with a microarray.

In some embodiments, the methods further comprise comparing the methylation profile of a nucleic acid with the copy number of the nucleic acid, thereby determining the contribution to a phenotype of the combination of the methylation of the nucleic acid and the copy number of the nucleic acid. In some embodiments, the copy number of the nucleic acid is detected with a microarray.

In some embodiments, the methods further comprise comparing the methylation profile of a specimen of a bacterial pathogen with a reference strain of the pathogen, wherein similarity of the methylation patterns indicates common origin of the specimen and the reference strain.

The present invention also provides polynucleotide microarrays. In some embodiments, the polynucleotide microarrays hybridize to first and a second labeled DNA portions, wherein the portions are from uniformly-sized populations of randomly cleaved or sheared DNA from a cell, tissue, or organism; wherein the first DNA portion comprises unmethylated and methylated DNA labeled with a first label; and wherein the second DNA portion is depleted for either unmethylated DNA or methylated DNA and the second portion of DNA is labeled with a second label different from the first label.

In some embodiments, the second test DNA portion is depleted for methylated DNA. In some embodiments, the second test DNA portion is depleted for unmethylated DNA. In some embodiments, the second DNA portion is depleted by treating the randomly cleaved or sheared DNA with a methyl-sensitive or methyl-dependent restriction enzyme and selecting uncleaved DNA.

In some embodiments, the DNA populations are from a plant. In some embodiments, the DNA populations are from an animal. In some embodiments, the DNA populations are from a fungus. In some embodiments, the DNA populations are from a prokaryote. In some embodiments, the prokaryote is a bacterial pathogen. In some embodiments, the bacterial pathogen is selected from the group consisting of gram negative and gram positive bacteria, which include *Listeria, E. coli, Salmonella, Yersinia*, and *Neisseria*, and mycobacteria. In some embodiments, the DNA populations are from a transgenic organism, cell, or tissue.

In some embodiments, the polynucleotide microarray comprises gene promoters and/or polynucleotide sequences which when methylated, silence neighboring gene expression.

The present invention also provides methods for producing an epigenetically uniform or diverse population of progeny from one or more parent individuals. In some embodiments, the method comprises the steps of:
 a. determining the genomic methylation profile of sexually or asexually propagated progeny of a parent individual; and
 b. selecting progeny exhibiting a uniform or diverse methylation profile, thereby producing an epigenetically uniform population from one or more parent individuals.

In some embodiments, the method further comprises determining the methylation profile of a parent individual and the selecting step comprises selecting progeny that exhibit the methylation profile of the parent individual. In some embodiments, the parent is an F1 hybrid. In some embodiments, the progeny are sexually propagated. In some embodiments, the progeny are asexually propagated. In some embodiments, the parent individual is a plant. In some embodiments, the parent individual is an animal. In some embodiments, the parent individual is a fungus. In some embodiments, the parent individual is a prokaryote. In some embodiments, the progeny are clones of the parent.

In some embodiments, the genomic methylation profile is determined on a solid support. In some embodiments, the solid support is a membrane. In some embodiments, the solid support is a methyl binding column. In some embodiments, the solid support is a microarray. In some embodiments, the solid support is a bead.

In some embodiments, the determining step comprises
 a. separating a sheared or randomly cleaved uniform DNA population into methylated and unmethylated fractions;
 b. labeling the methylated or unmethylated fractions with a first label; and
 c. hybridizing the methylated or unmethylated fractions to a nucleic acid.

In some embodiments, the method further comprises providing total genomic DNA labeled with a second label and hybridizing the total genomic DNA to a nucleic acid, thereby normalizing the signal from the first label.

In some embodiments, the genomic methylation profile of each individual or progeny is determined by the steps comprising:

a. providing a uniformly-sized population of randomly cleaved or sheared DNA from the cell, tissue, or organism, wherein the DNA comprises a first portion and a second portion and each portion comprises methylated and unmethylated nucleotides;
 b. labeling the first portion with a first label;
 c. depleting methylated or unmethylated DNA from the second portion;
 d. labeling the depleted second portion with a second label that is different from the first label;
 e. hybridizing the first portion and the depleted second portion to a nucleic acid;
 f. determining the relative methylation of the complementary nucleic acid fragments in the DNA by calculating the ratio of the two hybridizing labels, thereby determining the methylation profile of several such nucleic acid sequences from a cell, tissue, or organism.

In some embodiments, the method comprises the steps of:
 a. providing a uniformly-sized population of randomly cleaved or sheared DNA from the cell, tissue, or organism, wherein the DNA comprises a first portion and a second portion and the DNA comprises methylated and unmethylated recognition sequences of a methyl-sensitive or methyl-dependent restriction enzyme;
 b. labeling the first portion of the DNA population with a first label;
 c. cleaving the second portion with the methyl-sensitive or methyl-dependent restriction enzyme,
 d. depleting methylated or unmethylated DNA from the second portion;
 e. labeling uncleaved DNA from the second portion with a second label that is different than the first label;
 f. hybridizing the labeled DNA from the first and second portions to a nucleic acid; and
 g. determining the relative methylation of a nucleic acid by detecting the first and second labels hybridizing to the nucleic acid, thereby determining the methylation profile of the cell, tissue, or organism.

In some embodiments, the second portion is cleaved with a methyl-dependent restriction enzyme. In some embodiments, the second portion is cleaved with a methyl-sensitive restriction enzyme. In some embodiments, progeny are screened in groups.

The present invention also provides methods of associating heterosis with methylation profiles. In some embodiments, the method comprises crossing individuals to produce progeny; determining the methylation profile of the individuals and the progeny; and comparing a trait of the progeny with the methylation profiles of the individuals, thereby associating appearance of the trait with a methylation profile. In some embodiments, the individuals are from different heterotic groups.

The present invention provides methods for determining a methylation profile of a cell, tissue or organism. In some embodiments, the method comprises the steps of:
 a. providing a uniformly-sized population of randomly cleaved or sheared DNA from the cell, tissue or organism, wherein the DNA comprises a first portion and a second portion and each portion comprises methylated and unmethylated nucleotides;
 b. labeling the first portion with a first label;
 c. depleting methylated or unmethylated DNA from the second portion;
 d. labeling the depleted second portion with a second label that is different from the first label;
 e. hybridizing the first portion and the depleted second portion to a nucleic acid;

f. determining the relative methylation of the complementary nucleic acid fragments in the DNA by calculating the ratio of the two hybridizing labels, thereby determining the methylation profile of several such nucleic acid sequences from a cell, tissue, or organism.

In some embodiments, the second portion is depleted for methylated DNA. In some embodiments, the second portion is depleted for unmethylated DNA.

In some embodiments, the method comprises the steps of:
  a. providing a uniformly-sized population of randomly cleaved or sheared DNA from the cell, tissue, or organism, wherein the DNA comprises a first portion and a second portion and the DNA comprises methylated and unmethylated recognition sequences of a methyl-sensitive or methyl-dependent restriction enzyme;
  b. labeling the first portion of the DNA population with a first label;
  c. cleaving the second portion with the methyl-sensitive or methyl-dependent restriction enzyme,
  d. depleting methylated or unmethylated DNA from the second portion;
  e. labeling uncleaved DNA from the second portion with a second label that is different than the first label;
  f. hybridizing the labeled DNA from the first and second portions to a nucleic acid; and
  g. determining the relative methylation of a nucleic acid by detecting the first and second labels hybridizing to the nucleic acid, thereby determining the methylation profile of the cell, tissue, or organism.

In some embodiments, the second portion is cleaved with a methyl-sensitive restriction enzyme. In some embodiments, the second portion is cleaved with a methyl-dependent restriction enzyme.

In some embodiments, the nucleic acid is linked to a solid support. In some embodiments, the solid support is a microarray. In some embodiments, the solid support is a bead.

In some embodiments, the organism is a plant. In some embodiments, the organism is a fungus. In some embodiments, the organism is a prokaryote. In some embodiments, the prokaryote is a bacterial pathogen. In some embodiments, the bacterial pathogen is selected from the group consisting of gram negative and gram positive species, which include *Listeria, E. coli, Salmonella, Yersinia*, and *Neisseria*, and mycobacteria. In some embodiments, the organism is an animal. In some embodiments, the animal is a human. In some embodiments, the cell is a stem cell. In some embodiments, the cell is transgenic and the nucleic acid corresponds to the insertion site of a transgene. In some embodiments, the cell is a stem cell. In some embodiments, the cell is transgenic and the nucleic acid corresponds to the insertion site of a transgene. In some embodiments, the tissue is blood. In some embodiments, the tissue is biopsy tissue. In some embodiments, the tissue is resected tissue. In some embodiments, the tissue is normal. In some embodiments, the tissue is tumor tissue. In some embodiments, the tissue is precancerous.

In some embodiments, the method further comprises comparing the methylation profile of a nucleic acid with the transcription of the nucleic acid, thereby determining the relation between methylation and transcription of the nucleic acid. In some embodiments, the transcription of the nucleic acid is detected with a microarray. In some embodiments, further comprises comparing the methylation profile of a specimen of a bacterial pathogen with a reference strain of the pathogen, wherein similarity of the methylation patterns indicates common origin of the specimen and the reference strain.

DEFINITIONS

"Uniform" refers to a particular trait that shows little or no variation within a population. Typically, individuals within a uniform population will vary in a particular trait by no more than about 500% and in some cases will vary by as little as about 300%, 200%, 100%, 75%, 50%, 25%, 10%, 5% or 1% of the trait of a particular individual or the average individual in the population. Similarly, "uniform" or "uniformly-sized," when used in the context of DNA fragments in a DNA population, refers to a population with no more than about 500% variation (and in some cases as little as about 300%, 200%, 100%, 75%, 50%, 25%, 10%, 5% or 1% variation) in fragment length. For example, when the average length of a DNA fragments is 1,000 base pairs, a uniform population with 500% variation would have individuals with no more than 6,000 base pairs.

"Epigenetically uniform" refers to a population whose individual members have uniform epigenetic traits. For example, epigenetically uniform individuals will have little or no variation in methylation profiles between their genomes.

"Methylation" refers to cytosine methylation at positions $C^5$ or $N^4$ of cytosine, the $N^6$ position of adenine or other types of nucleic acid methylation.

"Separating" in the context of purification of nucleic acids from each other, refers to dividing nucleic acids in a mixture into two physically distinct populations. It is recognized that every member of one population need not be separated from the second population for separation to occur. For example, separating uncleaved unmethylated DNA from a second portion of DNA involves separating at least some unmethylated DNA into a separate population and typically involves separating a majority of the unmethylated DNA. Every uncleaved unmethylated DNA species need not be removed from the second portion for separating to occur. In another example, separating cleaved methylated DNA from a second portion of DNA involves separating at least some methylated DNA into a separate population and typically involves separating a majority of the methylated DNA. Every cleaved methylated DNA species need not be removed from the second portion for separating to occur. "Separating" is not limited to restriction cleavage and size separation, but also includes affinity purification as described herein and other methods known to those of skill in the art.

A "hybrid individual" refers to an individual who is the direct progeny resulting from the sexual cross of two parents or is otherwise a genetic composite of at least two individuals.

A "genome methylation profile" refers to a set of data representing the methylation state of DNA within the genome of an individual. The profile can indicate the methylation state of every base pair in an individual or can comprise information regarding a subset of the base pairs (e.g., the methylation state of specific restriction enzyme recognition sequence) in a genome. A number of methods for determining the methylation state of DNA are known in the art and are described herein.

The term "microarray" refers to an ordered arrangement of hybridizable array elements. The array elements are arranged so that there are preferably at least one or more different array elements, more preferably at least 100 array elements, and most preferably at least 1,000 array elements per $cm^2$ of substrate surface. Furthermore, the hybridization signal from each of the array elements is typically individually distinguishable.

A "methyl-dependent restriction enzyme" refers to a restriction enzyme (e.g., McrBC) that cleaves a methylated restriction sequence but does not cleave the same sequence when the sequence is unmethylated.

A "methyl-sensitive restriction enzyme" refers to a restriction enzyme (e.g., PstI) that cleaves an unmethylated restriction sequence but does not cleave the same sequence when the sequence is methylated.

A sample "depleted for methylated DNA" refers to DNA fragments from which a majority of the fragments containing methylated nucleotides at a sequence of interest (e.g., at a recognition site of a methyl-dependent restriction enzyme) have been removed. In some embodiments, a population depleted for methylated DNA contains no more than 40%, 30%, 20%, 10%, 5% or 1% fragments with at least one methylated sequence of interest. The remaining fragments in the depleted sample can contain methylated nucleotides in locations other than the sequence of interest.

A sample "depleted for unmethylated DNA" refers to DNA fragments from which a majority of the fragments containing unmethylated nucleotides at a sequence of interest (e.g., at a recognition site of a methyl-sensitive restriction enzyme) have been removed. In some embodiments, a population depleted for unmethylated DNA contains no more than 40%, 30%, 20%, 10%, 5% or 1% fragments with at least one unmethylated sequence of interest. The remaining fragments in the depleted sample can contain unmethylated nucleotides in locations other than the sequence of interest.

"Antibody" refers to a polypeptide substantially encoded by an immunoglobulin gene or immunoglobulin genes or fragments thereof, which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$—$C_H1$ by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially an Fab with part of the hinge region (see, Paul (Ed.) *Fundamental Immunology*, Third Edition, Raven Press, NY (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv).

"Heterosis" or "hybrid vigor" is manifested as an improved performance of an F1 hybrid in comparison to its two different inbred parents. Heterosis can be defined quantitatively as an upward deviation of the mid-parent, based on the average of the values of the two parents. See, e.g., Shull, G. 1909. Am Breed Assoc Rep 5:51-59/Johnson et al. *Genetics* 134(2): 465-474 (1993). For example, assume that two individuals from different breeds are mated which have weights of 30 and 40 lbs. Their progeny, if they weighed 50 lbs, performed at a level above each individual parent. The extra weight, defined as the difference between progeny performance level and the individual parents is assumed to be due to heterosis.

A "heterotic group" is a population of genotypes that, when crossed with individuals from another heterotic group or population, consistently outperform intra-population crosses. See, e.g., Hallauer, et al. QUANTITATIVE GENETICS IN MAIZE BREEDING (Iowa State Univ., Ames, Iowa 1988); Hallauer, et al., "Corn Breeding" In (ed.) CORN AND CORN IMPROVEMENT $3^{rd}$. (ASA-CSSA-SSSA, Madison, Wis. 1988), p. 463-564; Lee et al., *Crop. Sci.* 29, pp 1067-1071 (1989); Livini C., et al. *Theor. Appl. Genet.* 84, pp 17-25 (1992); Smith et al., *Maydica* 37, pp 53-60 (1992).

DETAILED DESCRIPTION OF THE INVENTION

1. Introduction

The effect of DNA methylation on gene expression is both regional and profound. Alterations in genomic methylation give rise to the inappropriate expression of neighboring genes. Consequently, the ability to survey the methylation states of multiple regions of the genome (or determine a 'methylation profile') allows for the association of specific methylation states with gene expression and or traits.

The present invention provides methods and compositions useful to identify and select individuals with similar or identical genomic methylation and thereby select a population of individuals that have desired phenotypes. These methods and compositions are useful, for example, for selecting individuals from a population (e.g., sexually or asexually propagated progeny) that retain desired traits. In addition, the methods and compositions are useful for identifying optimal mating pairs and optimal heterotic groups for the generation of progeny that have hybrid vigor. In addition, the methods and compositions are useful for the diagnosis of cancer, the identification of predictive biomarkers, and the discovery of new drug targets. The role of cancer and methylation is discussed in Jones & Baylin, *Nat Rev Genet.* 3(6):415-28 (2002).

This invention relies on routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al, eds., 1994)).

2. Determining Methylation Profiles

The present invention provides methods of determining methylation profiles of nucleic acids, including methylation profiles of entire genomes. The methods of the invention comprise generating a uniformly-sized population of fragmented (e.g., randomly cleaved or sheared) DNA and generating DNA samples consisting of methylated and/or unmethylated DNA. Methylation profiles of a nucleic acid can then be determined by quantifying the relative amounts of the nucleic acid between any two of the following: total DNA, methylated DNA or unmethylated DNA, i.e., samples depleted for unmethylated or methylated DNA, respectively.

Generally, these samples are generated by dividing the fragmented DNA into two equal portions (a "first portion" and a "second portion") and then separating the second portion into methylated and unmethylated DNA sub-portions.

The relative quantity of a fragment containing a nucleic acid sequence is then determined in any of:
  a. the first portion compared to the methylated DNA sub-portion;
  b. the first portion compared to the unmethylated DNA sub-portion; or
  c. the unmethylated DNA sub-portion compared to the methylated DNA sub-portion.
  d. the urmethylated DNA sub-portion compared to the methylated DNA sub-portion compared to the first portion.

Fragmented DNA

As discussed above, in many embodiments, the starting genomic DNA is fragmented. Fragmentation can be performed by any method known to those of skill in the art (e.g., mechanically sheared, cleaved with a restriction enzyme or DNase I, etc.). In some embodiments, a uniformly-sized population of fragments is isolated (e.g., by agarose gel electrophoresis and elution of a particular range of fragment sizes). For example, the average size of the fragments can be, e.g., about 0.1, 0.5, 1, 2, 3, 4, 5 kb or more. In some embodiments, the average size of the fragments ranges between, e.g., 0.1-1, 1-2, 1-3, 1-5, 2-4, or 1-10 kb.

Separating Methylated and Unmethiylated DNA

A number of methods can be used to separate DNA into methylated or unmethylated DNA sub-portions.

In some embodiments, this can be achieved, for example, by cleaving the fragmented genomic DNA of a uniform length with a methyl-sensitive (or alternatively a methyl-dependent) restriction endonuclease to separate one or two sub-portions: a sub-portion of uncleaved DNA molecules and a sub-portion of cleaved DNA molecules. When methyl-dependent restriction enzymes are used (cleaving methylated sequences but not unmethylated sequences), the sub-portion of uncleaved DNA fragments will represent unmethylated restriction sequences and the sub-portion of cleaved DNA fragments will represent methylated restriction sequences. Conversely, when a methyl-sensitive restriction enzyme is used (cleaving unmethylated sequences but not methylated sequences), the sub-portion of uncleaved DNA fragments will represent methylated restriction sequences and the sub-portion of cleaved DNA fragments will represent unmethylated restriction sequences.

A number of methyl-dependent and methyl-sensitive restriction enzymes are known to those of skill in the art. Restriction enzymes can generally be obtained from, e.g., New England Biolabs (Beverly, Mass.) or Roche Applied Sciences (Indianapolis, Ind.). Exemplary methyl-dependent restriction enzymes include, e.g., McrBC, McrA, MrrA, and Dpnl. Exemplary methyl-sensitive restriction enzymes include, e.g., PstI, BstNI, FseI, MspI, CfoI, and HpaII. See e.g., McClelland, M. et al, Nucleic Acids Res. 1994 September; 22(17):3640-59 and http://rebase.neb.com.

The two sub-portions of DNA molecules (i.e., cleaved and uncleaved populations) can be separated by molecular weight using a number of methods known to those of skill in the art. For example, gel electrophoresis, size exclusion chromatography, size differential centrifugation (e.g., in a sucrose gradient) can be used to separate cleaved fragments from heavier uncleaved fragments.

Those of skill in the art will recognize that other methods of separating methylated and unmethylated populations, thereby depleting the sample of methylated or unmethylated DNA, can also be used. For example, antibodies or other agents (e.g., MeCP2) specific for methylated nucleic acids or proteins associated with methylated nucleic acids can be used to affinity purify the methylated nucleic acids, thereby separating the methylated DNA from unmethylated DNA. See, e.g., Meehan, et al., *Nucleic Acids Res.* 20(19):5085-92 (1992). In this case, the DNA can, but need not, be cleaved with a restriction endonuclease that senses methylation. In some embodiments, for example, an affinity column comprising a protein specific for methylated DNA is used to separate methylated and unmethylated fractions. Once separated into fractions, either fraction or both fractions can be labeled for hybridization.

In other embodiments, chemical agents, alone or in concert with enzymes, capable of specifically cleaving methylated nucleic acids are used to generate methylated and unmethylated populations. The populations can then be separated as described above.

Pre-Amplification of the Sub-Portions

Once DNA fragments have been separated into a first portion comprising total DNA and methylated DNA and unmethylated DNA sub-portions, there are a number of ways known to those of skill in the art to uniformly amplify the fragments in each sub-portion before any specific nucleic acid is quantified within the sub-portions. For example, pre-amplification of the fragments will boost the signal from any specific nucleic acid within a sub-portion and will allow the methylation profiling of specific sequences in trace amounts of starting DNA present. Such techniques are useful when only small samples of genomic DNA are available, such as in samples from biopsy tissue or resected tumors. In one example, double stranded DNA adapters are ligated to DNA fragment ends in the sub-portions. Oligonucleotides specific to the DNA adapters are then added to each sub-portion and the population of DNA fragments in the sub-portion is then amplified using linear (e.g., rolling circle) or exponential (e.g. PCR) DNA amplification techniques, for example.

Quantifying DNA

Quantification of a nucleic acid in the DNA samples (i.e., the first portion, the methylated DNA sub-portion and/or the unmethylated sub-portion) can be performed by any method known to those of skill in the art.

Hybridization

For example, simple hybridization can be used to quantify the nucleic acid sequence in the DNA samples. In one example, the two or more samples are labeled with different labels (e.g., fluorescent or otherwise detectable labels) and the relative signals of the different labels are determined by standard methods following hybridization of the labeled samples to the nucleic acid. Hybridization of a given DNA probe to a particular methylated sequence indicates that the sequence is methylated. Absence of probe hybridization indicates that the sequence is not methylated. Similarly, unmethylated DNA from an individual can be used as a target, wherein hybridization indicates that the sequence is not methylated in the individual.

In some embodiments, the samples are hybridized to probes on a microarray. This embodiment is particularly useful for determining the methylation profile of a large number of sequences, including, e.g., a set of sites that comprise the entire genome.

In some embodiments, the hybridization of methylated DNA to a given probe and unmethylated DNA to a given probe will be measured, and these measurements will be compared to each other. This allows, for example, a determination of the relative hybridization intensity of unmethylated and methylated target DNA at a given probe.

In some embodiments, the hybridization to a given probe of the methylated or unmethylated sub-portions will be measured and compared with the measured hybridization to a given probe of total genomic DNA, i.e., the "first portion."

Total genomic DNA acts as a reference to normalize data from the hybridization of the methylated or unmethylated DNA sub-portions. This allows, for example, a determination of relative hybridization intensities at a given probe between methylated target DNA and total target DNA. In cases where the total target DNA hybridizes to more than one sequence in the genome, hybridization of total target DNA allows for a determination of how many copies of the sequence hybridize. If hybridization of the methylated DNA results in only a fraction of the signal produced by the total DNA target, then the user can calculate which fractions of hybridizing sequences are methylated.

A probe nucleic acid represents the nucleic acid sequence to which the target(s) are hybridized. Typically, the probe nucleic acid is at least a fragment of genomic DNA. Differential hybridization (as determined by monitoring the two or more different labels) indicates the relative methylation at a particular genomic sequence.

Probe nucleic acids can be any sequence. In some embodiments, a number of different target nucleic acids are probed, thereby providing information about the methylation state of each target. In some embodiments, probe nucleic acids represent known methylation sites or other nucleic sequences of interest (e.g., a sequences whose methylation is associated with a phenotype such as cancer). Alternatively, probe nucleic acids are random or expressed sequences.

To process information about a large number of DNA sequences (i.e., probes) in the genome, it can be convenient to hybridize the two labeled populations to a microarray or other addressed array of probes. The number of probes screened can be, e.g., at least about 2, 5, 10, 20, 50, 100, 500, 1000, 10000 or more fragments. In some embodiments, the probe nucleic acids are displayed on a solid support. Exemplary solid supports include, e.g., beads or a microarray. In some embodiments, the target sequences are displayed on a solid support.

For the purposes of the following discussion, probes refer to nucleic acids elements on a microarray and target nucleic acids refer to methylated or umnethylated nucleic acid fractions or total genomic nucleic acids. When probes are employed as hybridizable array elements on a microarray, the array elements are organized in an ordered fashion so that each element is present at a specified location on the substrate. Because the array elements are at specified locations on the substrate, the hybridization patterns and intensities, including differential hybridization of targets (which together create a unique expression profile) can be interpreted in terms of methylation profiles and can be correlated with a phenotype (e.g., hybrid vigor or cancer).

The differential hybridization of total DNA and methylated DNA, total DNA and unmethylated DNA, unmethylated DNA and methylated DNA, or total DNA and methylated DNA and unmethylated DNA can be analyzed. For differential hybridization, at least two different target DNA samples are prepared and labeled with different labeling moieties. The mixture of the two or more labeled DNA samples is added to a microarray. The microarray is then examined under conditions in which the emissions from each of the two or more different labels are individually detectable.

In some embodiments, the labels are fluorescent labels with distinguishable emission spectra, such as a lissamine-conjugated nucleotide analog and a fluorescein conjugated nucleotide analog. In another embodiment, Cy3/Cy5 fluorophores (Amersham Pharmacia Biotech) are employed. For instance, for microarray applications, it can be convenient to use fluorescent labels (e.g., Cy3 or Cy5) that are readily detected. However, those of skill in the art will recognize that any type of detectable label can be employed (e.g., radioactive, fluorescent, enzymatic, or other methods known to those of skill in the art).

After hybridization, the microarray is washed to remove nonhybridized nucleic acids, and complex formation between the hybridizable array elements and the probes is detected. Methods for detecting complex formation are well known to those skilled in the art. As discussed above, in some embodiments, the target polynucleotides are labeled with a fluorescent label, and measurement of levels and patterns of fluorescence indicative of complex formation is accomplished by fluorescence microscopy, such as confocal fluorescence microscopy. An argon ion laser excites the fluorescent label, emissions are directed to a photomultiplier, and the amount of emitted light is detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance of each hybridized target polynucleotide.

In a differential hybridization experiment, target polynucleotides from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained.

Typically, microarray fluorescence intensities can be normalized to take into account variations in hybridization intensities when more than one microarray is used under similar test conditions. In some embodiments, individual polynucleotide probe/target complex hybridization intensities are normalized using the intensities derived from internal normalization controls contained on each microarray or from the intensity of hybridization of total genomic DNA.

Quantitative Amplification

Nucleic acid sequences within a DNA sample (e.g., the first portion of a sub-portion) can also be determined by any of a number of quantitative amplification techniques known to those with skill in the art (e.g., quantitative PCR or quantitative linear amplification). Methods of quantitative amplification are disclosed in, e.g., U.S. Pat. Nos. 6,180,349; 6,033,854; and 5,972,602, as well as in, e.g., Gibson et al., *Genome Research* 6:995-1001 (1996); DeGraves, et al., *Biotechniques* 34(1):106-10, 112-5 (2003); Deiman B, et al., *Mol Biotechnol.* 20(2):163-79 (2002).

One method for detection of amplification products is the 5' nuclease PCR assay (also referred to as the TaqMan™ assay) (Holland et al., *Proc. Natl. Acad. Sci. USA* 88: 7276-7280 (1991); Lee et al., *Nucleic Acids Res.* 21: 3761-3766 (1993)). This assay detects the accumulation of a specific PCR product by hybridization and cleavage of a doubly labeled fluorogenic probe (the "TaqMan™." probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if, and only if, it hybridizes to the segment being amplified. Cleavage of the probe generates an increase in the fluorescence intensity of the reporter dye.

Another method of detecting amplification products that relies on the use of energy transfer is the "beacon probe" method described by Tyagi and Kramer (*Nature Biotech.* 14:303-309 (1996)), which is also the subject of U.S. Pat. Nos. 5,119,801 and 5,312,728. This method employs oligonucleotide hybridization probes that can form hairpin structures. On one end of the hybridization probe (either the 5' or 3' end), there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in hairpin (closed) conformation, the fluorescence of the donor fluorophore is quenched. When employed in PCR, the molecular beacon probe, which hybridizes to one of the strands of the PCR product, is in "open conformation," and fluorescence is detected, while those that remain unhybridized will not fluoresce (Tyagi and Kramer, *Nature Biotechnol* 14: 303-306 (1996). As a result, the amount of fluorescence will increase as the amount of PCR product increases, and thus may be used as a measure of the progress of the PCR. Those of skill in the art will recognize that other methods of quantitative amplification are also available.

Additional Methylation Profiling Methods

Methylation profiles can be detected in a number of additional ways known to those of skill in the art. For example, simple hybridization analysis (e.g., Southern blotting) of nucleic acids cleaved with methyl-sensitive or methyl-dependent restriction endonucleases can be used to detect methylation patterns. Typically, these methods involve use of one or more targets that hybridize to at least one sequence that may be methylated. The presence or absence of methylation of a restriction sequence is determined by the length of the polynucleotide hybridizing to the probe. This and other methods for detecting DNA methylation, such as bisulfite sequencing, are described in, e.g., Thomassin et al., *Methods* 19(3):465-75 (1999).

3. Uses of Methylation Profiling

A. General Methods

Methylation profiling is useful to predict any phenotype associated with a particular methylation pattern. Once such a relationship is established, methylation profiling is an efficient method for identifying individual cells or organisms that have a desired phenotype. For example, methylation profiles can be associated with agrinomically useful traits in plants or animals, or in the medical field, with specific cancer types, thereby allowing for diagnosis or treatment.

Association of a desired phenotype with a methylation pattern can occur in any number of ways. In a simple example, the particular phenotype of an individual (e.g., a cell or organism) is desired in a population (e.g., progeny or clones of the individual). In such cases, the methylation profile of the individual is determined and individuals in the population are selected that have the same or similar profile as the individual with the desired phenotype. Alternatively, a particular methylation profile may be avoided by selecting individuals that lack a methylation profile of parent cell or organism. In other embodiments, progeny or clones are selected to have methylation patterns different from any parent.

A useful method for correlating desired phenotypes with methylation profiles involves determining a correlation of methylation with transcription. Thus, transcription of one or a set of transcripts is determined for different individuals or cells and then transcription is correlated with a particular methylation pattern. Transcription can be determined by any method known to those of skill in the art. Particularly useful methods for determining the transcription of a large number of genes involves microarray (e.g., "GeneChip") analysis.

In addition, methylation profiling methods of the present invention can be combined with comparative genome hybridization (CGH). CGH is a method for detecting deletions and amplifications in one sample of genomic DNA relative to another individual sample. This is done by comparing the intensity of hybridization of microarray features to each target sample, each labeled with different fluorescent dyes.

CGH can be combined with methylation profiling methods of the present invention because one of the targets labeled for hybridization to the microarray is a sample of total DNA, which can be compared to another such sample from another methylation profiling experiment.

In this application, genomic DNA from two different individuals, cell lines, or organisms, for example, are sheared or randomly cleaved to create uniformly-sized DNA fragments. A portion (e.g., half) of each sample is then digested with a methylation sensitive or methylation dependent enzyme, as described herein. All four samples are then refragmented to isolate total DNA and either methylated or unmethylated DNA sub-portionss from each individual. These four samples can then be hybridized to a nucleic acid, e.g., a microarray. In some embodiments, the four samples are labeled with four different labels (e.g., fluorescent dyes). The ratio of total DNA samples provides the CGH profile, while the ratio of depleted and total samples provides the methylation profile from each individual.

Alternatively, the labeled samples can be hybridized in alternating pairs to the microarrays. In such a design, each of the samples is labeled with each of two dyes, allowing for simultaneous analysis of all the samples for deletions and methylation changes. This type of analysis is sometimes referred to as a loop design (see, e.g., Craig, et al. 2001. "Designing microarray experiments: chips, dips, flips, and skips" in PROCEEDINGS OF APPLIED STATISTICS IN AGRICULTURE, 2001 (Ed. George Milliken)).

An example of such a design is illustrated below. In the example below, the two individuals are represented as A and B.

| Array Hybridization Experiment Number | Cy3 | Cy5 |
|---|---|---|
| 1 | A | A depleted |
| 2 | A depleted | B |
| 3 | B | B depleted |
| 4 | B depleted | A |

In this design, each sample is labeled with each dye, allowing relative dye incorporation to be taken into account. Only four arrays are used, thus minimizing the amount of time and resources required to analyze methylation profile differences across a whole genome between individuals. Alternatively, using four different dyes would allow the same data to be generated from hybridization of a single array.

B. Selecting Desired Populations

Epigenetically uniform populations can be identified and selected by determining the methylation profile of individuals and then selecting those individuals with similar profiles. These methods are useful, for example, to isolate asexual clones of an individual with a desired phenotype, thereby identifying clones with the same phenotype. In some embodiments, at least about 80%, 85%, 90%, 95%, 98%, or 99% of the selected clones have a methylation profile substantially identical to the asexual parent.

Clones or progeny with a methylation profile similar or identical to an individual with a desired phenotype (e.g., hybrid vigor) are likely to have the desired phenotype. Where asexual progeny are produced from an individual (e.g., via asexual propagation of a vigorous hybrid plant or animal, by nuclear transplantation, micropropagation, by cell division of stem cells, etc.), the clones are genetically identical to the individual, but differ epigenetically. By selecting clones with methylation profiles similar or identical to the hybrid, one can select clones that maintain the vigorous phenotype of the hybrid. Asexually propagated progeny are genetically identical to the hybrid. Therefore, the methods described herein are useful for identifying asexual progeny that are genetically and epigenetically the same and therefore have the same phenotype as the parent.

Those of skill in the art will recognize that the uniformity of the selected population of clones will depend on how similar the profile between the hybrid and the population of selected clones is. For example, the user can decide that absolute identity with the hybrid at all loci is not required and therefore progeny can be selected that have a desired percentage of loci that are identical. For example, clones can be selected if at least about 50%, 60%, 70%, 80%, 90%, 95%, 98%, 99% or 100% of the loci measured have the same methylation state as the hybrid. Alternatively, the quality of individual loci can be monitored in a population (e.g., progeny) to determine the relative importance of particular loci in hybrid vigor. In this case, the user may choose to select clones that have complete identity important loci known to control or affect the desired phenotype, while allowing for at least some, and sometimes complete, variance at other loci.

Individuals can be screened according to the methods of the invention individually, or in groups (i.e., pools). Grouping of individuals allows for rapid processing of large numbers of individuals.

The invention can be used over a broad range of organisms, including fungi, animals and plants. For example, any agricultural organism can be used. Exemplary animals are those where animal husbandry has been employed, including pigs, bovine, poultry, other birds, horses, zoo animals, nearly extinct species, and the like.

The invention has use over a broad range of plants, including species from the genera *Anacardium, Arachis, Asparagus, Atropa, Avena, Brassica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panieum, Pannesetum, Persea, Phaseolus, Pistachia, Pisum, Pyrus, Prunus, Raphanus, Ricinus, Secale, Senecio, Sinapis, Solanum, Sorghum, Theobromus, Trigonella, Triticum, Vicia, Vitis, Vigna,* and *Zea.* Once clones or progeny are selected, they can be cultivated, thereby producing a crop of plants displaying a uniform desired trait.

In one embodiment, the methylation profile of asexually propagated plants (e.g., palms) is used to select a uniform population comprising plants with similar or identical methylation patterns.

The present invention can also be used to screen cell populations for desired phenotypes. Exemplary cells include stem cells, including adult or fetal stem cells, or any other cell or organism where somaclonal variation can occur within a population. Thus, the present invention allows one to monitor for the presence of variation and to select individuals that have or lack that variation. Similarly, cancer cell methylation profiles can be determined for use, e.g., in diagnosis and treatment.

In another embodiment, transgenic cells or organisms are screened to determine the effect, if any, of a transgene on methylation. Methylation profiles of these individuals can be determined genome-wide or can be determined in a region of the genome flanking the insertion of the transgene. This method can be used, for example, to efficiently select transformants most likely to not carry deleterious mutations or chromosomal effects caused by transgene insertion.

C. Further Uses in Breeding

Traditional breeding techniques can be improved by determining the methylation profile of potential breeding pairs. By associating methylation patterns with heterotic traits, breeders can select breeding pairs that will generate the desired methylation pattern in progeny and therefore result in vigorous progeny.

In addition, methylation profiles, or individual sequences, can be identified and used to design optimal pairs. Heterotic groups are populations of individuals that, when crossed with individuals from another heterotic group or population, consistently outperform intra-population crosses. By comparing methylation states associated (i.e., linked) to each heterotic group, and determining the profiles of progeny displaying hybrid vigor, methylation profiles can be determined for optimal breeding pairs. Once a methylation profile is determined for a particular heterotic group, new individuals within the group can be determined without extensive crossing.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill will readily recognize a variety of non-critical parameters that could be changed or modified to yield essentially similar results.

Example 1

Determination of Methylation Profiles

Twenty micrograms of total genomic DNA is sheared to a size range of 1-10 kb. The sheared DNA is divided into two equal parts, one of which is digested to completion with 80 units of mcrBC for at least 12 hours at 37 C. The purpose of the nebulization is to randomly shear the genomic DNA such that the entire genome is represented equally in all fragment sizes 1 kb-10 kb. In addition, the small fragment sizes also facilitate gel-purification and Cy-dye incorporation (see below). The two samples are then fragmented on a 0.8% agarose gel along with size standards. Gel slices in the size range of 1 kb and greater are then excised, and the DNA purified using Qiagen Qiaquick gel extraction spin columns according to the manufacturers protocol.

Digested and undigested gel purified samples are labeled with Cy3 and Cy5 respectively using the Megaprime DNA labeling Kit, Amersham Pharmacia and hybridized to microarrays in 3×SSC 0.3% SDS at 65 C overnight. Slides are washed after 12-16 hours in 1×SSC 0.1% SDS (1×) and 0.2×SSC (2×) at 50 C, and then scanned using a commercial scanner, such as Axon Instruments Genepix Pro 4000A Dual Laser Scanner.

After background and other corrections, the ratio of signal intensity in the Cy3 and Cy5 channels is calculated. Dye swap analysis is used to take account of experimental variation, by repeating the hybridization with identical samples labeled with Cy5 and Cy3, respectively.

Digestion with mcrBC removes methylated DNA from the size fraction, reducing the signal after labeling and hybridization. Thus the ratio of Cy5 to Cy3 represents the relative methylation at the sequence represented by the spot on the microarray. This procedure allows high copy repeated sequences to be analyzed at the same time as low copy ones, as the ratio takes copy number into account.

Approximately 50 μg of total RNA is isolated using standard methods. The RNA is then converted to first strand cDNA using oligo-dT or random primers. The converted cDNA is labeled with Cy3/Cy5 using commercially available random priming kits. The fluorescently labeled cDNA is then hybridized to a microarray containing the genes of interest, washed and scanned using conditions similar to those described above. After background and other corrections, the ratio of signal intensity in the Cy3 and Cy5 channels is calculated. Dye swap analysis is used to take account of experimental variation, by repeating the hybridization with identical samples labeled with Cy5 and Cy3, respectively, and correlations with DNA methylation in the identical regions can be established by comparing the chip obtained data sets.

Example 2

Correlation of Methylation Profiles with Transcription

The methylation profile of a 1.7 Mb stretch of the *Arabidopsis thaliana* heterochromatic knob region on chromosome 4 was established using the techniques specified in Example 1. Here, we demonstrate that the DNA methylation pattern of this region correlated with its pattern of gene expression. We also show, using mutation analysis, that genetically altering the pattern of DNA methylation for the region profoundly alters the pattern of gene-expression from the locus. Finally, we show that chromatin modification in the region (measured by a different analysis) independently confirms our correlation of DNA methylation and gene expression.

*Arabidopsis* chromosome 4 contains a heterochromatic region or knob on the short arm. We amplified sequential 1 kb amplicons spanning the knob region and generated a deposition micro-array representing the region. We determined the methylation profile of the region, as well as association with modified histones (H3K9) which are enriched in silent DNA. Finally, we measured gene expression and determined the transcriptional profile for the region.

Methylation profiles were determined as described in Example 1. Briefly, genomic DNA was nebulized to a constant size and then depleted of methylated DNA via digestion with mcrBC. Large fragments, representing unmethylated DNA were purified. Undigested and digested DNA were purified and each labeled with a different label and hybridized to a microarray representing the genome on chromosome 4. The ratio of hybridization targets was then determined.

The effect of methylation loss within our knob region upon both gene expression and chromatin state was examined. We chose to use ddm1 mutations to de-methylate our region of interest. ddm1 mutations hypomethylate genomic DNA through the disruption of a chromatin remodeling complex related to SWI/SNF. See, e.g., Jeddeloh et al., *Nat Genet.* 22(1):94-7 (1999).

We determined that heterochromatin is de-repressed in ddm1. Using the methods described above, we construct a map of the entire 1.7 Mb knob region of chromosome 4. Positions and transcriptional direction of predicted genes were determined. The amount of DNA methylation was detected using methylation profiling by position through the region. In addition, the amount of transcription was detected for each position throughout the region, revealing only a handful of active genes which were also unmethylated.

The transcriptional profile by position was also obtained from ddm1 mutant plants. In contrast to wild type plants, the ddm1 mutants expressed a large number of the open reading frames in the region, mostly corresponding to transposons.

Chromatin immunoprecipitation (ChIP) was also performed on the wild-type and mutant plants. Chromatin immunoprecipitation involved the following steps.

Young seedlings were treated with formaldehyde and protein-DNA and protein-protein interactions were fixed by in vivo cross-linking. Chromatin was extracted, sonicated, immunoprecipitated, and eluted. The eluant was treated to reverse the cross-linking and DNA was purified from the eluant. The resulting DNA was analyzed by PCR and Southern/microarray analysis.

Using these methods, protein constituents of chromatin were identified and their abundance quantified on a per sequence basis. Histone H3 (H3) was methylated at either Lysine 4 or Lysine 9. Modification by methylation at either specifies different fates for the molecule. H3mK4 is abundant in expressed genes, and H3mK9 is abundant in transcriptionally silent genes. Genomic regions containing H3mK9 have been shown highly compacted, unlike the loosely packaged H3mH4.

Using the data derived as described above, we determined that histone methylation correlates with DNA methylation. Methylated histone H3 (mK9) was excluded from incorporation into expressed genes. Similarly, methylated histone H3 (mK4) was excluded from silent genes. In the wild-type plant, expressed genes in the region were associated with H3mK4. The silent genes only contained H3mK9.

We also determined that heterochromatic DNA methylation correlates with histone H3 lysine-9 methylation. The DNA methylation state closely matched the chromatin packaging state of the genomic DNA.

Heterochromatic H3mK9 and DNA methylation were coordinately lost in ddm1 mutants. The ddm1 mutants lost both the methylation signal and the chromatin packaging signal.

In total, these data demonstrate that identifying the methylation profile of a particular genome, or region of the gene imparts both gene expression and chromatin packaging state information about the loci. Transcriptional profiling will assist in verifying the gene expression data and identifying the extent of correlation. ChIP can provide similar information, but is much more labor-intensive and requires more data manipulation to determine the extent of correlation.

Example 3

Detection of DNA/DNA Hybridization to Microarrays of a Large, Complex Genome

Female placental human genomic DNA (Sigma) was sheared using a GeneMachines Hydroshear to a uniform size range between 1 and 4 Kb: The DNA was isolated from low-melt agarose gel slices following electrophoresis. The concentration of eluted DNA was measured using a Nanodrop scanning spectrophotometer. Approximately 1 μg of the DNA was random-prime labeled using the direct incorporation of Cy3-dCTP with the Bioprime-kit (Invitrogen), and a parallel reaction incorporated Cy5-dCTP. The labeled DNAs were purified following the synthesis reaction, and the incorporation of the Cy dyes was monitored using the spectrum-scanning 1000 (NanoDrop). The hybridization cocktail contained both synthesis reactions, unlabelled human C0t-1

DNA to suppress background (Invitrogen), Agilent/Operon positive control oligonucleotides, and oligonucleotides to suppress hybridization to any poly-A (or T) present on the cDNAs. The Agilent human 1 catalog cDNA array was hybridized overnight according to Agilent instructions at 65° C.

The arrays were then washed three times, using five-minute incubations, in varying amounts of SSC and SDS. The arrays were air dried in a centrifuge, and then scanned using the Agilent scanner and software (vA6.1). The hybridization intensity of each feature was extracted from the TIFF files using the Agilent feature extraction software (v A6.1). The data files were then imported into Genespring 5.0 (Silicon Genetics) for visualization. The experiment was performed upon three arrays and the Lowess normalized (spot-to-spot and array-to-array normalization) and averaged data set was determined.

The array contains 18,560 features, representing 12,814 ESTs (the ~5000 remaining features are Agilent's proprietary controls). The results demonstrate that detection of coding sequence using labeled whole human-genome targets is possible. Overall, 5.5% (1,022/18,560 features) of the probes yielded poor performance, since measured fluorescence intensity less than 100 U in either channel. However, within this set of 1,022 features, only 260 were actually ESTs, while the remaining 762 were Agilent control features. Poor performing genic features represented only 2% of those on the array (260/12,814). Because the data follows the 1.0 expectancy across a broad signal range (3 logs), the experiments were deemed a success.

Example 4

Methylation Profiling Using DNA Microarrays

The methylation profiling technique was applied to the same human female placental genomic DNA. Methylation profiling predicts methylation (red) when the ratios deviate from the 1.0 line (dark-blue) and t-tests revealed that more than 75% of the features had acceptably small standard deviations (SD). These observations suggest the technique is reproducibly detecting sequences that are methylated in the human genome.

In the methylation profiling experiments, only 845 features gave poor performance, as previously defined. Poorly performing features represented only 1.2% of the total ESTs on the array (148/12814). As before, the majority of the EST signal intensity fell across nearly 3 logs, indicating large differences in copy number.

Example 5

Biological Relevance of Human Methylated Alleles Detected by the Methods of the Invention If the methylation profiling works as predicted, then the dye ratio signals should be altered by in vitro pretreatment of the DNA with methylases, thereby artificially increasing 5 mC content. Methylation profiling was performed upon human female placental genomic DNA that had been subjected to a three-point methylase cocktail time-course (0 min, 3 min, and 15 min @ 1 U/μg). The DNAs were exposed to M.SssI, which transfers a methyl group to cytosines in CpG sequences, and M.MspI, which similarly transfers methyl groups to the outer cytosine of genomic CCGG sites (http://rebase.neb.com). Quantitative determination was tested by selecting time points before the methylase reaction reached completion. The procedure was performed as described previously, though without a dye-swap. The untreated sample was labeled red (Cy5) for each array. The results of the same 1,500 features on the four different arrays clearly demonstrates that the methylation profiling methods of the invention detected an increasing presence of methylation within a series of DNA samples methylated in vitro. In addition, many loci contain endogenous methylation. Table 1 lists the top 16 loci.predicted to contain methylation within the female placental genome.

TABLE 1

5mC containing feature predictions from female placenta

| Locus | Description | GenBank | 5mC Ratio (NT/5mC depleted-)* | t-test p-value** | 5mC flags |
|---|---|---|---|---|---|
| 10760 | T cell receptor gamma locus | AI972955 | 1.895 (1.417 to 2.38) | 7.33E−08 | P |
| 16191 | Human chromosome 3, olfactory receptor pseudogene cluster 1, complete sequence, and myosin light chain kinase (MLCK) pseudogene, partial sequence. | AF042089 | 2.123 (1.898 to 2.34) | 7.57E−08 | P |
| 5567 | P311 protein | NM_004772 | 1.834 (1.44 to 2.248) | 2.57E−06 | P |
| 3258 | DKFZP566C134 protein | AB040922 | 1.862 (1.439 to 2.295) | 3.48E−06 | P |
| 2192 | olfactory receptor, family 7, subfamily E, member 12 pseudogene | AK021566 | 1.595 (1.13 to 1.879) | 1.59E−05 | P |
| 3873 | retinoblastoma-binding protein 6 | X85133 | 1.625 (1.222 to 2.197) | 1.89E−05 | P |
| 12149 | ribosomal protein L10a | AI133371 | 1.577 (1.213 to 2.065) | 3.21E−05 | P |
| 2317 | Human cell surface glycoprotein CD44 (CD44) gene, exon 6. | L05411 | 1.566 (1.251 to 1.903) | 6.44E−05 | P |
| 15420 | activin A receptor, type I | L02911 | 1.642 (1.33 to 1.938) | 7.89E−05 | P |
| 2601 | glutamic-oxaloacetic transaminase 1, soluble (aspartate aminotransferase 1) | NM_002079 | 1.758 (1.335 to 2.224) | 8.16E−05 | P |
| 18152 | chimerin (chimaerin) 1 | X51408 | 1.542 (1.29 to 1.862) | 8.78E−05 | P |
| 17302 | antigen identified by monoclonal antibody Ki-67 | X65550 | 2.055 (1.354 to 3.351) | 1.29E−04 | P |
| 1240 | asparaginyl-tRNA synthetase | NM_004539 | 1.489 (1.237 to 1.621) | 1.45E−04 | P |
| 13099 | zinc finger protein 236 | AF085244 | 1.735 (1.285 to 2.398) | 1.63E−04 | P |
| 12161 | Incyte EST | 0 | 1.533 (1.254 to 2.091) | 1.87E−04 | P |

TABLE 1-continued

5mC containing feature predictions from female placenta

| Locus | Description | GenBank | 5mC Ratio (NT/5mC depleted-)* | t-test p-value** | 5mC flags |
|---|---|---|---|---|---|
| 1845 | Human chromosome 3, olfactory receptor pseudogene cluster 1, complete sequence, and myosin light chain kinase (MLCK) pseudogene, partial sequence. | AF042089 | 1.471 (1.203 to 1.678) | 1.93E–04 | P |

*Table 1 lists average (n = 8 (4 dye-swaps)) 5mC intensity ratios obtained from each feature were sorted by T-test P-value, and then by overall ratio. The ratio reflects the average intensity obtained from the untreated dye channel divided by the methylation depleted dye channel. The ratio range is also indicated.
**The t-test p-value was determined by utilizing the signal channel precision, (the SD of pixel hybridization intensity/feature) within GeneSpring (v 5.0). As such, the table shows the feature identity and the corresponding methylation ration from the 16 most reproducibly obtained measurements.

By examining the annotation of the features in Table 1, interesting and biologically-relevant loci were apparent. For instance, the T-cell gamma receptor gene family and the olfactory receptor-pseudogene-cluster locus were easily identified. T-cell receptor loci contain a large amount of DNA methylation that is essential for proper T-cell receptor function (Dennis, K., et al., *Genes Dev* 15(22):2940-4 (2001); Geiman, T. M., et al., *Biochim Biophys Acta* 1526(2):211-20 (2001); Geiman, T. M. and K. Muegge, *Proc Natl AcadSci USA* 97(9): p. 4772-7 (2000)).

The second interesting locus is the olfactory receptor-pseudogene-cluster. Pseudogene clusters would be expected to contain methylated sequences because the pseudogenes are transcriptionally silent. Moreover, in mice, the expressed olfactory receptor alleles and associated gene clusters have been demonstrated to be susceptible to epigenetic gene-silencing in a parent-of-origin specific manner (Ishii, T., et al., *Genes Cells* 6(1):71-8 (2001)). A third sequence corresponded to a CpG island which was previously cloned by virtue of its methylation in male blood (Cross, S. H., et al., *Nat Genet,* 6(3): p. 236-44 (1994)). Different features from the same pseudogene cluster displayed different ratios, indicating the quantitative nature of the assay. Individual loci predicted to contain methylation were then verified by an independent method.

To statistically test feature performance, the intensity ratios from methylation profiling were averaged by feature performance during a self-self experiment as an indicator of inherent noise in the system. Modeling in this manner is not optimal since governing probe performance can be different in each experiment. The data were re-plotted. Two loci were selected from this data set that were predicted to contain 5mC, T cell receptor, ratio=1.38; p-values=0.019, and CpG island clone Z62622, ratio=1.26; p-value=0.017. Two loci predicted not to contain methylation, also CpG island clones, were also selected, Z65427, ratio=1.03; p-value=0.99, and Z59762, ratio=0.91; p-value=0.87. The GenBank accession for each locus was retrieved, and PCR primers were selected that would afford amplification of the 3' most exon of each genomic target.

For independent verification, female placental genomic DNA was subjected to partial digestion with McrBC and amplified using primers from methylated and unmethylated regions of the genome. PCR reactions were established with similar McrBC-digested template concentrations and were amplified for a similar number of cycles. Theoretically, the number of products derived from unmethylated sequences should remain constant, while the number of products derived from methylated sequences should decrease in proportion to the amount of McrBC digestion. The results from parallel duplicate analyses nicely confirmed that methylated loci predicted by methylation profiling are, in fact, endogenously methylated. Similarly, loci predicted by methylation profiling to not be endogenously methylated were independently confirmed to be unmethylated.

In conclusion, within the human genome, the methylation profiling methods of the invention showed quantitative detection of in vitro methylated and qualitative detection of endogenous DNA methylation of the genome.

What is claimed is:

1. A method for determining the relative amount of methylated or unmethylated DNA comprising a nucleic acid sequence of interest, wherein the DNA is from a cell, tissue or organism, the method comprising the steps of:
   a. providing a population of randomly cleaved or sheared DNA fragments from the cell, tissue, or organism, wherein the DNA comprises methylated and unmethylated fragments;
   b. depleting methylated or unmethylated DNA from the population; and
   c. quantifying the amount of the nucleic acid sequence of interest in the methylated DNA in the depleted population or the amount of the nucleic acid sequence of interest in the unmethylated DNA in the depleted population relative to the amount of the sequence in total genomic DNA.

2. The method of claim 1, wherein the average size of the DNA fragments is between 0.1-10 kb.

3. The method of claim 1, wherein the depleting step comprises:
   fragmenting the population with a methylation-sensitive restriction enzyme or a methylation-dependent restriction enzyme to produce digested DNA and undigested DNA; and
   separating the digested DNA from the undigested DNA.

4. The method of claim 1, wherein the methylated DNA is depleted from the randomly cleaved or sheared DNA.

5. The method of claim 1, wherein the unmethylated DNA is depleted from the randomly cleaved or sheared DNA.

6. The method of claim 1, wherein the organism is selected from a plant, an animal, a fungus, and a prokaryote.

7. The method of claim 1, wherein the method further comprises comparing the methylation profile of a nucleic acid with a transcription profile of the nucleic acid, thereby determining the relation between methylation profile and the transcription profile of the nucleic acid.

8. The method of claim 1, wherein the method further comprises comparing the methylation profile of a nucleic acid with a chromatin packaging state profile of the nucleic acid, thereby determining the relation between methylation profile and the chromatin packaging state profile of the nucleic acid.

9. The method of claim 1, further comprising comparing the methylation profile of the nucleic acid with the copy number of the nucleic acid, thereby determining the contribution to a phenotype of the combination of the methylation of the nucleic acid and the copy number of the nucleic acid.

10. The method of claim 1, wherein the quantifying step (c) comprises a quantitative amplification reaction.

11. The method of claim 1, wherein the sequence is of a size of 0.1 kb or greater.

12. The method of claim 1 further comprising quantifying the amount of a second sequence on interest in the methylated DNA in the depleted population or the amount of the sequence in the unmethylated DNA in the depleted population relative to the amount of the second sequence in total genomic DNA.

13. The method of claim 1, wherein the cell, tissue, or organism is from an animal.

14. The method of claim 13, wherein the animal is a human.

* * * * *